(12) United States Patent
Mateos et al.

(10) Patent No.: US 10,106,518 B2
(45) Date of Patent: Oct. 23, 2018

(54) CHROMENE DERIVATIVES AS INHIBITORS OF TCR-NCK INTERACTION

(71) Applicant: ARTAX BIOPHARMA INC., Cambridge, MA (US)

(72) Inventors: Andrés Gagete Mateos, Cambridge, MA (US); Julio Castro Palomino, Barcelona (ES); Luc Marti Clauzel, Cambridge, MA (US); Damiá Tormo Carulla, Cambridge, MA (US)

(73) Assignee: Artax Biopharma Inc., Cambridge, MA (US)

( * ) Notice: Subject to any disclaimer, the term of this patent is extended or adjusted under 35 U.S.C. 154(b) by 68 days.

(21) Appl. No.: 15/029,061

(22) PCT Filed: Oct. 20, 2014

(86) PCT No.: PCT/IB2014/002177
§ 371 (c)(1),
(2) Date: Apr. 13, 2016

(87) PCT Pub. No.: WO2015/056086
PCT Pub. Date: Apr. 23, 2015

(65) Prior Publication Data
US 2016/0251330 A1    Sep. 1, 2016

(30) Foreign Application Priority Data
Oct. 18, 2013   (ES) .................................. 201331543

(51) Int. Cl.
*C07D 311/58* (2006.01)
*C07D 311/60* (2006.01)
*C07D 405/06* (2006.01)
*C07D 405/12* (2006.01)

(52) U.S. Cl.
CPC .......... *C07D 311/58* (2013.01); *C07D 311/60* (2013.01); *C07D 405/06* (2013.01); *C07D 405/12* (2013.01)

(58) Field of Classification Search
CPC .................................................. C07D 405/02
USPC ......................................................... 544/376
See application file for complete search history.

(56) References Cited

U.S. PATENT DOCUMENTS

| 8,614,231 | B2 | 12/2013 | Sanchez et al. |
| 9,120,764 | B2 | 9/2015 | Sanchez et al. |
| 2012/0135041 | A1* | 5/2012 | Alarcon Sanchez ......... A61K 31/453 424/278.1 |
| 2014/0005247 | A1* | 1/2014 | Alarcon Sanchez ......... C07D 311/58 514/422 |
| 2016/0244423 | A1* | 8/2016 | Mateos ................. C07D 311/74 |

FOREIGN PATENT DOCUMENTS

| EP | 2354134 A1 | 8/2011 |
| EP | 2623503 | * 8/2013 |
| EP | 2623503 A1 | 8/2013 |
| WO | 2001034591 | 5/2001 |
| WO | 0208217 A2 | 1/2002 |
| WO | 2002092076 | 11/2002 |
| WO | 03062272 A1 | 7/2003 |
| WO | 2003096982 A2 | 11/2003 |
| WO | 2007115820 A1 | 10/2007 |
| WO | 2010000900 A1 | 1/2010 |
| WO | 2010009069 A1 | 1/2010 |
| WO | 2010064707 A1 | 6/2010 |
| WO | 2012042078 A1 | 4/2012 |

OTHER PUBLICATIONS

American Diabetes Association, "Complications", http://www.diabetes.org/living-with-diabetes/complications/, accessed Dec. 27, 2017 (Year: 2017).*
Mayo Clinic, "Diabetes", https://www.mayoclinic.org/diseases-conditions/diabetes/symptoms-causes/syc-20371444, accessed Dec. 27, 2017 (Year: 2017).*
Kannan et al., Pathophysiology, 2005, vol. 12., No. 3, pp. 167-181 (Year: 2005).*
Asquith et al., Eur.J.Immunol., 2009, vol. 39, No. 8, pp. 2040-2044 (Year: 2009).*
Moudgil et al., Curr. Rheumatol. Rep., 2011, vol. 13, No. 5, pp. 456-463 (Year: 2011).*
Spanish International Search Report dated Jan. 20, 2015 for International Application No. 201331543 filed Oct. 18, 2013.
Francesco Leonetti et al; "Design, Synthesis, and 3D QSAR of Novel Potent and Selective Aromatase Inhibitors", Journal of Medicinal Chemistry, vol. 47, No. 27 Dec. 1, 2004 (Dec. 1, 2004), pp. 6792-6803, XP055096789, ISSN: 0022-2623, DOI: 10.1021/jm049535j *tables 3, 4; compound 32*.

(Continued)

*Primary Examiner* — Jeffrey S Lundgren
*Assistant Examiner* — Stephanie K Springer
(74) *Attorney, Agent, or Firm* — Andrea L. C. Reid; Dechert LLP (57) ABSTRACT

The present invention relates to a group of compounds of formula (I) containing a chromene nucleus:

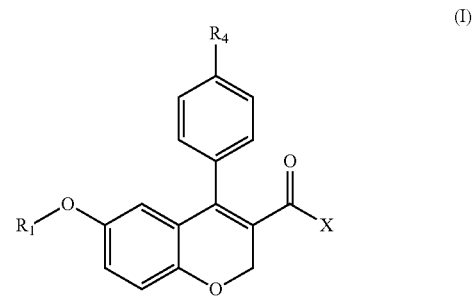

and which present the ability to inhibit the lymphocytes proliferation mediated by the TCR interaction with Nck, so that the present invention also relates to the use of these compounds for the treatment of diseases or conditions wherein said interaction triggers a complication such as transplant rejection reactions, immune or autoimmune diseases, inflammatory diseases or proliferative diseases.

20 Claims, 1 Drawing Sheet

(56) References Cited

OTHER PUBLICATIONS

PCT International Search Report dated Jan. 12, 2015 for International Application No. PCT/IB2014/002171, filed Oct. 20, 2014.
Spanish Search report dated Jan. 20, 2015 for International Application No. 201331542, filed Oct. 18, 2013.
Alarcon et al., "Initiation of TCR signaling: regulation within CD3 dimers," Immunological Reviews, vol. 191, No Month Listed 2003 (pp. 38-46).
Borie et al., "Combined Use of the JAK3 Inhibitor CP-690,550 with Mycopenolate Mofetil to Prevent Kidney Allograft Rejection in Nonhuman Primates," Transplanation, vol. 80, No. 12, Dec. 27, 2005 (pp. 1756-1764).
Cetkovic-Cvrlje and Uckun, "Targeting Janus kinase 3 in the treatment of leukemia and inflmmatory diseases," Archivum Immunologiae et Therapiae Experimentalis, vol. 52, No. 2, Mar.-Apr. 2004 (pp. 69-82).
Cetkovic-Cvrlje and Tibbles, "Theraputic Potential of Janus Kimase 3 (JAK3) Inhibitors," Current Pharmaceutical Design, vol. 10, No. 15, No Month Listed 2004 (pp. 1767-1784).
Das et al., "Discovery and SAR of 2-amino-5-(thioaryl)thiazoles as potent and selective ltk inhibitors," Bioorganic & Medicinal Chemistry, vol. 25, No. 4, Apr. 1982 (pp. 393-397).
Gil et al., "Recruitment of Nck by CD3e Reveals a Ligand-Induced Conformational Change Essential for T Cell Receptor Signaling and Synapse Formation," Cell, vol. 109, Jun. 28, 2002 (pp. 901-912).
Glennon and Liebowitz, "Serotonin Receptor Affinity of Cathinone and Related Analogues," Journal of Medicinal Chemistry, vol. 25, No. 4, Apr. 1982 (pp. 393-397).
Holmdahl et al., "Collagen induced arthritis as an experimental model for rheumatoid arthritis," APMIS, vol. 97, No. 7, Jul. 1989 (pp. 575-584).
International Search Report issued by the Spanish Patent and Trademark Office as Searching Authority for International Paten Application No. PCT/ES2013/31543, dated Jan. 20, 2015 (4 pages).
Kaur et al., "Inhibitors of interleukin-2 inducible T-cell kinase as potential therapeutic candidate for the treatment of various inflammatory disease conditions," European Journal of Pharmaceutical Sciences, vol. 47, No. 3, Oct. 2102 (pp. 574-588).
Kremer et al., "A Randomized, Double-Blind, Placebo-Controlled Trial 3 Dose Levels of CP-690,550 Versus Placebo in the Treatment of Active Rheumatoid Arthritis," American College of Rheumatology, 2006 Annual Scientific Meeting, Presentation No. L40, retrieved online <<https://acr.confex.com/acr/2006webprogram/Paper6207.html>> accessed on Nov. 29, 2017 (2 pages).
Kudlacz et al., "The Novel JAK-3 Inhibitor CP-690550Is a Potent Immunosuppressive Agen in Various Murine Models," American Journal of Transplantation, vol. 4, No. 1, Jan. 2004 (pp. 51-57).
Lin and Weiss, "T cell receptor signalling," Journal of Cell Science, vol. 114, No. 2, Jan. 2001 (pp. 243-244).
Malaviya et. al., "Targeting Janus Kinase 3 in Mast Cells Prevents Immediate Hypersensitivity Reactions and Anaphylaxis," The Journal of Biological Chemistry, vol. 274, No. 38, Sep. 17, 1999 (pp. 27028-27038).
Malaviya et. al., "Treatment of Allergic Asthma by Targeting Janus Kinase 3-Dependent Leukotriene Synthesis in Mast Cells with 4-(3',5'-Dibromom-4'-hydroxyphenypamino-6,7-dimethoxyquinazole (WHI-P97)," The Journal of Pharmacology and Experimental Therapeutics, vol. 295, No. 3, No Month Listed 2000 (pp. 901-926).
Matsumoto et al., "IgE Hyperproduction Through Enhanced Tyrosine Phosphorylation of Janus Kinase 3 in NC/Nga Mice, a Model for Human Atopic Dermatitis," The Journal of Immunology, vol. 162, No Month Listed 1999 (pp. 1056-1063).
Milici et al., "Cartilage Preservation by Inhibition of Janus Kinase 3 (JAK3) in a Murine Collagen-Induced-Arthritis (CIA) Model and Rat Adjuvant-Arthritis (AA) Model," American College of Rheumatology, 2006 Annual Scientific Meeting, Presentation No. 789, retrieved online <<https://acr.confex.com/acr/2006/webprogram/Paper4156.html>>.
Muller-Ladner et al., "Activation of the IL-4 STAT Pathway in Rheumatoid Synovium," The Journal of Immunology, vol. 164, No Month Listed 2000 (pp. 3894-3901).
Narla et al., "Inhibition of Human Glioblastoma Cell Adhesion and Invasion by 4-(4'-Hydroxylphenyl)-amino-6,7-dimethoxyquinazoline (WHI-P131) and 4-(3'-Bromo-4'-hydroxylphenyl)-amino-6,7-dimethoxyquinazoline (WHI-P154)," Clinical Cancer Research, vol. 4, Oct. 1998 (pp. 2463-2471).
O'Shea et al., "A New Modality for Immunosuppression: Targeting the JAK/STAT Pathway," Drug Discovery, vol. 3, Jul. 2004 (pp. 555-564).
Paniagua et al., "Effects of JAK3 Inhibition with CP-690,550 on Immune Cell Populations and Their Functions in Nonhuman Primate Recipients of Kidney Allograft," Transplantation, vol. 80, No Month Listed 2005 (pp. 1283-1292).
Rousvoal et al., "Janus kinase 3 inhibition with CP-690,550 prevents allograft vasculopathy," European Society for Organ Transplantation, vol. 19, No Month Listed 2006 (pp. 1014-1021).
Roy et al., "Nck adaptors are positive regulators of the size and sensitivity of the T-cell repertoire," Proceedings of the National Academy of Science of the United States of America, vol. 107, No. 34, Aug. 2010 (pp. 15529-15534).
Saemann et al., "Janus kinase-3 (JAK3) inhibition: a novel immunosuppressive option for allogeneic transplantation," Transplant International, vol. 17, No. 9, Oct. 2004 (pp. 481-489).
Silva et al., "Immunotherapy for De Novo Renal Transplantation," Drugs, vol. 66, No. 13, No Month Listed 2006 (pp. 1665-1684).
Sudbeck et al., "Structure-based Design of Specific Inhibitors of Janus Kinase 3 as Apoptosis-inducing Antileukemic Agents," Clinical Cancer Research, vol. 5, Jun. 1999 (pp. 1569-1582).
Tibbles et al., "Role of a JAK3-dependent Biochemical Signaling Pathway in Platelet Activation and Aggregation," The Journal of biological Chemistry, vol. 276, No. 21, May 25, 2001 (pp. 17815-17822).
Trieu et al, "A Specific Inhibitor of Janus Kinase-3 Increases Survival in a Transgenic Mouse Model of Amyotrophic Lateral Sclerosis," Biochemical and Biophysical Research Communications, vol. 267, No. 1, No Month Listed 2000 (pp. 22-25).
Walker et al., "Changes in synovial tissue Jak-STAT expression in rheumatoid arthritis in response to successful DMARD treatment," Annals of the Rheumatic Diseases, vol. 65, No. 12, Dec. 2006 (pp. 1558-1564).
Higuchi, Takao. Prevention of Acute Lung Allograft Rejection in Rat by the Janus Kinase 3 Inhibitor, Tyrphostin AG490, The Second Department of Surgery and Department of Biochemistry, Fukuoka University School of Medicine, Fukuoka University School of Medicine, Fukuoka, Japan, Nov. 13, 2004, Copyright 2005 by the International Society for Heart and Lung Transplantation.
International Search Report dated Octber 5, 2009 in re PCT/ES2009/070239, filed on Jun. 18, 2009.
Database Registry, RN 340014-88-2, Retrieved from STN international [online]; retrieved on Jul. 8, 2013, Japanese Office Action of Japanese Application 2011-515490 dated Jul. 16, 2013.
Gonzalez-Rey et al., "Theraputic Effect of Vasoactive Intestinal Peptide on Experimental Autoimmune Encephalomyelitis," American Journal of Pathology, vol. 168 No. 4, Apr. 2006 (1179-1188).

\* cited by examiner

CHROMENE DERIVATIVES AS INHIBITORS OF TCR-NCK INTERACTION

The present invention relates to a group of compounds containing a chromene core and that have the ability to inhibit lymphocyte proliferation by blocking the interaction of TCR with Nck, therefore such compounds are useful for treating diseases or conditions where such interaction triggers a complication such as transplant rejection reactions, immune or autoimmune diseases or proliferative diseases.

STATE OF THE ART

Autoimmune and inflammatory diseases such as asthma, multiple sclerosis, allergies, rheumatoid arthritis, Crohn's disease or psoriasis are a diverse group of diseases in which the adaptive immune system, particularly via T lymphocytes attack the body's own antigens. It is commonly accepted that T cells are at the center of all immunological mechanisms. T cells can recognize both foreign and self-antigens and activate the immune response against them. T cells recognize antigens via the T cell receptor (TCR), responsible for the transmission of signals to the cytoplasm. Indeed, the fact that the haplotype of the major histocompatibility complex (MHC) is the most important genetic risk factor to the human autoimmune diseases places T-cells in the center of all immunopathological events.

The T cell recognizes the antigen peptide associated with MHC (pMHC) via the T cell antigen receptor (TCR) and is able to translate the small differences in the chemical composition of the pMHO into different quantitative and qualitative results. While a variety of control mechanisms to prevent activation of T cells bearing TCRs with significant affinity for MHC loaded with self-peptides exists, including suppression of potentially auto-reactive T cells during maturation in the thymus, these mechanisms are somewhat insufficient in patients that develop autoimmune diseases and auto-reactive T cells are activated and expand, overcoming homeostatic controls.

Upon stimulation, the TCR is activated and undergoes a conformational change that results in the recruitment of different proteins forming the "TCR signalosome" responsible for signal transduction and cell activation. This complex includes the cytosolic protein Nck that binds to a PRS motif (proline-rich sequence) present in the CD3ε subunit of the T cell receptor. As a result, the TCR conformational change stabilizes and the activation signal is efficiently transmitted.

Current therapies for immune diseases appear as immunosuppressive strategies rather than tolerogenic/immunomodulatory approaches. Azathioprine, methotrexate, mycophenolate and cladribine are cytostatic. Other therapies force the depletion of T cells (Alemtuzumab, anti-CD52) or their retention in lymph nodes (Fingolimod). Alternatively, indirect modulation of the immune system is also being used as a powerful strategy (BG-12). Therefore, despite the central role of TCR signal for activating T cells in autoimmune diseases, recent efforts to modulate activation of the T cells are focused in modulating co-stimulatory signals, cytokine receptors, etc. with the consequent lack of specificity and a large number of associated side effects.

In order to develop a specific immunomodulatory therapy, many efforts have been focused on characterizing the role of Nck in T cell activation by means of many different research groups. Nck has been attributed an important role in the function of mature T cells through studies in knock-out mice lacking Nck1 in all tissues and lacking Nck2 conditionally only on T cells. In these models, the number of peripheral T cells expressing a TCR with low avidity for self antigens fell sharply, and a general deterioration in the activation of T cells by stimulation with weak antigens was observed. Moreover, the importance of Nck was also addressed by generating bone marrow chimeras showing that the PRS motive (Nck binding site in the TCR) is important for the activation of mature T cells by weak agonists but not strong ones. Similarly, mutation of the PRS sequence altered the ability of mice to activate an adaptive immune response in vivo. Furthermore, an inhibitor peptide with high affinity for the SH3.1 domain of Nck alters the assembly of the TCR signalosome, suggesting that the recruitment of Nck is a critical early step in TCR signalling, which represents a target for the modulation of the immune response.

The document WO2010/064707 describes a series of compounds derived from 2H-chromene for the prevention or treatment of an disease induced by an undesired lymphocytes infiltration mediated by the sphingosine-1-phosphate receptor (S1P1).

The document WO2012/042078 also describes chromene derivatives with inhibitory capacity of the TCR-Nck interaction in T cells and their use for the treatment of autoimmune diseases, inflammatory diseases or transplant rejection.

It would therefore be desirable to provide novel compounds which are capable of inhibiting TCR-Nck interaction in T lymphocytes, and that are a good drug candidate. The compounds should exhibit good activity on in vivo pharmacological trial, good oral absorption when administered orally as well as being metabolically stable and having a favourable pharmacokinetic profile. Moreover, compounds should not be toxic and present minimal side effects.

DESCRIPTION OF THE INVENTION

The first aspect of the present invention relates to a compound of formula (I)

or a pharmaceutically acceptable salt, isomer or solvate thereof wherein:

$R_1$ is selected from hydrogen, substituted or not substituted $C_1$-$C_6$ alkyl, substituted or not substituted $C_3$-$C_8$, substituted or not substituted aryl or substituted or not substituted heteroaryl, —$COR_5$, —$C(O)OR_5$, —$C(O)NR_5R_6$, —$CNR_5$;

X is selected from —OH or —$NR_2R_3$;

$R_2$ and $R_3$ are independently selected from hydrogen, substituted or not substituted $C_1$-$C_6$ alkyl, substituted or not substituted $C_3$-$C_6$ cycloalkyl, substituted or not substituted aryl, substituted or not substituted heteroaryl, —$COR_7$, —$C(O)OR_7$, —$C(O)NR_7R_8$, —$CNR_7$, —$OR_7$, —$NR_7R_8$ and —$NR_7C(O)R_8$;

or $R_2$ and $R_3$ form, together with the nitrogen atom they are bound to, a substituted or not substituted heterocycle;

$R_4$ is halogen;

$R_5$, $R_6$, $R_7$ and $R_8$ are independently selected from hydrogen, $C_1$-$C_4$ alkyl, $C_3$-$C_6$ cycloalkyl, aryl, heteroaryl and halogen.

Another aspect of the present invention relates to a compound of formula (II):

(II)

or a pharmaceutically acceptable salt, isomer or solvate thereof wherein:

$R_1$ is selected from hydrogen, substituted or not substituted $C_1$-$C_6$ alkyl, substituted or not substituted $C_3$-$C_6$ cycloalkyl, substituted or not substituted aryl or substituted or not substituted heteroaryl, —$COR_5$, —$C(O)OR_5$, —$C(O)NR_5R_6$, —$CNR_5$;

$R_2$ and $R_3$ are independently selected from hydrogen, substituted or not substituted $C_1$-$C_6$ alkyl, substituted or not substituted $C_3$-$C_6$ cycloalkyl, substituted or not substituted aryl, substituted or not substituted heteroaryl, —$COR_7$, —$C(O)OR_7$, —$C(O)NR_7R_8$, —$CNR_7$, —$OR_7$, —$NR_7R_8$ and —$NR_7C(O)R_8$;

or $R_2$ and $R_3$ form, together with the nitrogen atom they are bound to, a substituted or not substituted heterocycle;

$R_4$ is halogen;

$R_5$, $R_6$, $R_7$ and $R_8$ are independently selected from hydrogen, $C_1$-$C_4$ alkyl, $C_3$-$C_6$ cycloalkyl, aryl, heteroaryl and halogen.

The term "alkyl" refers, in the present invention, to radicals of hydrocarbonated chains, linear or branched, having 1 to 6 carbon atoms, and preferably 1 to 4, and bound to the rest of the molecule by a single bond, for example, methyl, ethyl, n-propyl, i-propyl, n-butyl, tert-butyl, sec-butyl, n-pentyl, n-hexyl, etc. The alkyl groups may be optionally substituted by one or more substituents such as halogen, hydroxyl, alkoxyl, carboxyl, carbonyl, cyano, acyl, alkoxycarbonyl, amino, nitro, mercapto and alkylthio.

The term "cycloalkyl" refers, in the present invention, to a stable 3 to 6-membered monocyclic radical, preferably 3-membered, saturated or partially unsaturated, and which consists only of carbon and hydrogen atoms, such as cyclopropyl, cyclopentyl, cyclohexyl and which may optionally be substituted by one or more groups such as alkyl, halogen, hydroxyl, alkoxyl, carboxyl, cyano, carbonyl, acyl, alkoxycarbonyl, amino, nitro, mercapto and alkylthio.

The term "aryl" refers, in the present invention, to an aromatic carbocyclic chain having 6 to 18 carbon atoms, preferably 6 to 14 carbon atoms and more preferably 6 to 8, and may be made of a single or multiple rings in the latter case with separated and/or fused rings. Nonlimiting examples of the aryl group are phenyl, naphthyl, indenyl, etc. Preferably the aryl group is a phenyl or naphthyl. The aryl groups may be optionally substituted by one or more substituents such as alkyl, halogen, hydroxyl, alkoxyl, carboxyl, carbonyl, cyano, acyl, alkoxycarbonyl, amino, nitro, mercapto and alkylthio.

The term "heteroaryl" refers to an aryl group containing at least one heteroatom selected from the following group: nitrogen, oxygen or sulfur.

The term "heterocycle" refers, in the present invention, to a stable monocyclic or bicyclic radical of 3 to 15 members that is unsaturated, saturated or partially saturated, and which consists of carbon atoms and at least one heteroatom selected from the following group: nitrogen, oxygen or sulfur. Preferably, it has 4 to 8 members with one or more heteroatoms, more preferably from 5 to 6 members with one or more heteroatoms. Examples of heteroaryl may be, not limited to: azepines, indoles, imidazoles, isothiazoles, thiadiazoles, furan, tetrahydrofuran, benzimidazole, benzothiazole, piperidine, pyrrolidine, piperazine, purine, quinoline. Preferably, the heterocyclic group is pyrrolidine or piperazine. The heterocycle groups may be optionally substituted in any of their positions by one or more substituents such as alkyl, halogen, hydroxyl, alkoxyl, carboxyl, carbonyl, cyano, acyl, alkoxycarbonyl, amino, nitro, mercapto and alkylthio.

"Halogen" refers to fluorine, chlorine, bromine or iodine.

In a preferred embodiment, $R_1$ is a substituted or not substituted $C_1$-$C_4$ alkyl.

In a more preferred embodiment, $R_1$ is —$CH_3$.

In another more preferred embodiment, $R_1$ is a $C_1$-$C_4$ alkyl substituted by a $C_3$-$C_6$ cycloalkyl. In an even more preferred embodiment, $R_1$ is a —$CH_2$-cyclopropyl group.

In another preferred embodiment, $R_2$ is H.

In another preferred embodiment, $R_3$ is a substituted or not substituted $C_1$-$C_4$ alkyl.

In a more preferred embodiment, $R_3$ is a —$CH_2CH_3$ group.

In another more preferred embodiment, $R_3$ is a $C_1$-$C_4$ alkyl substituted by a group —NR'R", wherein R' and R" are independently selected from H or $C_1$-$C_4$ alkyl. In another even more preferred embodiment, $R_3$ is the —$CH_2$—$CH_2$—$N(CH_3)_2$ group.

In another preferred embodiment, $R_2$ and $R_3$ form a substituted or not substituted saturated 5-membered heterocyclic.

In another preferred embodiment, $R_2$ and $R_3$ form a substituted or not substituted saturated 6-membered heterocycle.

In another more preferred embodiment, the saturated heterocycle is substituted by a $C_1$-$C_4$ alkyl in at least one of its positions.

In another more preferred embodiment, the saturated 6-membered heterocycle contains inserted an additional not substituted N atom or substituted by a $C_1$-$C_4$ alkyl.

In another preferred embodiment, $R_3$ is a saturated 6-membered heterocycle containing an additional inserted N atom not substituted or substituted by a $C_1$-$C_4$ alkyl.

In another preferred embodiment, $R_4$ is fluorine.

In another preferred embodiment, the compound of formula (I) is selected from the following list:

(4-(4-fluorophenyl)-6-methoxy-2H-chromene-3-yl)(pyrrolidin-1-yl)methanone,

N-ethyl-4-(4-fluorophenyl)-6-methoxy-2H-chromene-3-carboxamide, (4-(4-fluorophenyl)-6-methox-2H-chromene-3-yl)(4-methylpiperazin-1-yl)methanone, N-(2-(dimethylamino)ethyl-4-(4-fluorophenyl)-6-methoxy-2H-chromene-3-carboxamide, (6-(cyclopropylmethoxy)-4-(4-fluorophenyl)-2H-chromene-3-yl)(pyrrolidin-1-yl)methanone,
6-(cyclopropylmethoxy)-N-ethyl-4-(4-fluorophenyl)-2H-chromene-3-carboxamide, and
(6-(cyclopropylmethoxy)-4-(4-fluorophenyl)-2H-chromene-3-yl)(4-methylpiperazin-1-yl)methanone,
(6-(cyclopropylmethoxy)-4-(4-fluorophenyl)-2H-chromene-3-yl)(pyrrolidin-1-yl)methanone,
6-(cyclopropylmethoxy)-N-ethyl-4-(4-fluorophenyl)-2H-chromene-3-carboxamide,
(6-(cyclopropylmethoxy)-4-(4-fluorophenyl)-2H-chromene-3-yl)(4-methylpiperazin-1-yl)methanone,
6-(cyclopropylmethoxy)-N-(2-(dimethylamino)ethyl)-4-(4-fluorophenyl)-2H-chromene-3-carboxamide In another preferred embodiment X is an —OH.

In another preferred embodiment, the compound of formula (I) is the 4-(4-fluorophenyl)-6-methoxi-2H-chromene-3-carboxylic acid Another aspect of the invention relates to the use of the compound of formula (I) as described above for the manufacture of a medicament.

Another aspect of the invention relates to the use of the compound of formula (I) as described above for the manufacture of a medicament for treating diseases or disorders mediated by TCR-Nck interaction in T lymphocytes.

Throughout this description, the terms "treatment" of a disease, "treat" a disease or other grammatically related expressions refer to a curative treatment as well as a palliative treatment or prophylactic treatment of such disease.

In a preferred embodiment, the disease or disorder mediated by the TCR-Nck interaction in T lymphocytes is selected among transplant rejection, immune, autoimmune and inflammatory diseases, neurodegenerative diseases, hematological diseases and proliferative diseases.

In a more preferred embodiment, the disease or disorder mediated by the TCR-Nck interaction in T lymphocytes is selected from transplant rejection, rheumatoid arthritis, psoriatic arthritis, psoriasis, Type I diabetes, complications associated with diabetes, multiple sclerosis, systemic lupus erythematosus, atopic dermatitis, mast cell-mediated allergic reactions, leukemias, lymphomas and thromboembolic and allergic complications associated with leukemias and lymphomas.

Another aspect of the invention refers to a compound of formula (I) for its use in the treatment of diseases or disorders mediated by the TCR-Nck interaction in T lymphocytes.

Another aspect of the invention relates to a pharmaceutical composition comprising a compound of formula (I) as described above and one or more pharmaceutically acceptable excipients.

The compounds described in the present invention, its pharmaceutically acceptable salts and/or solvates like the pharmaceutical compositions that contain them can be used together with other additional drugs to provide a combination therapy. Said additional drugs can be part of the same pharmaceutical composition or, alternatively, can be provided in form of a separate composition for its simultaneous administration or not to the pharmaceutical composition comprising a compound of formula (I), or an isomer, solvate or a salt pharmaceutically acceptable thereof.

Unless otherwise indicated, the compounds of the invention also include compounds which differ only in the presence of one or more isotopically enriched atoms. For example, compounds having said structure, except for the replacement of a hydrogen by a deuterium or tritium, or the replacement of a carbon by a $^{13}C$ or $^{14}C$-enriched carbon or a $^{15}N$-enriched nitrogen, are within the scope of this invention.

The compounds of formula (I) for therapeutic use are prepared in solid form or aqueous suspension, in a pharmaceutically acceptable diluent. These preparations may be administered by any suitable route of administration, for which said preparation will be formulated in the pharmaceutically adequate method for the chosen route of administration. In a particular embodiment, administration of the compound of formula (I) provided by this invention is carried out by oral, topical, rectal or parenteral (including subcutaneous, intraperitoneal, intradermal, intramuscular, intravenous, etc.) route. A review of the different pharmaceutical forms of administering medicaments and of excipients necessary for obtaining them can be found, for example, in the "Treaty of Galenic Pharmacy" C. Faulí i Trillo, 1993 Luzán 5, SA Ediciones, Madrid, or in other common or similar to the Spanish, European or American Pharmacopoeias.

For its application in therapy, the compounds of formula (I), their isomers, salts or solvates, will be found, preferably, to be in a acceptable or substantially pure pharmaceutical form, i.e., having a pharmaceutically acceptable level of purity excluding pharmaceutical additives that are normal such as diluents and carriers, and not including material considered toxic at levels of normal dosage. The purity levels for the active substance are preferably above 50%, more preferably above 70%, more preferably greater than 90%. In a preferred embodiment, they are above 95% of the compound of formula (I), or of its isomers, salts or solvates.

The compounds of the invention may be in crystalline form as free compounds or as solvates and it is intended that both forms are within the scope of the present invention. Here, the term "solvate" as used herein, includes both pharmaceutically acceptable solvates, i.e. solvates if the compound of formula (I) which can be used in the manufacture of a medicament, as pharmaceutically unacceptable solvates, which may be useful in the preparation of salts or solvates that are pharmaceutically acceptable. The nature of the pharmaceutically acceptable solvate is not critical provided that it is pharmaceutically acceptable. In a particular embodiment, the solvate is a hydrate. The solvates may be obtained by conventional methods of solvation well known by technicians of the subject.

The compounds of the present invention represented by formula (I), and specifically, the specific compounds belonging to this general formula described previously may include isomers, depending on the presence of multiple bonds (e.g. Z, E), including optical isomers or enantiomers, depending on the presence of chiral centers. The isomers, enantiomers or individual diastereoisomers and mixtures thereof fall within the scope of the present invention. The individual enantiomers or diastereoisomers, like their mixtures, may be separated by conventional techniques.

Another aspect of the invention is a method of treating diseases or disorders mediated by the TCR-Nck interaction in T cells which comprises administering a therapeutically effective amount of a compound of formula (I) to a patient in need thereof.

As used herein, the term "therapeutically effective amount" refers to the amount of active compound sufficient to produce the desired effect in which the symptoms of the disease are attenuated. The dose should not be used in amounts that cause unwanted side effects, in which clinical assessment makes them adverse and them therapeutically untreatable. Generally the dosage will vary with the age, condition, sex and extent of disease in the patient as well as the route and frequency of administration and will be determined in each case.

Another aspect of the invention relates to a process of obtaining a compound of formula (I) as described above comprising the following steps:

a) reacting a compound of for la (II) with a compound of formula (III) and a compound of formula (IV)

wherein $R_1$, X and $R_4$ have the same meaning as in claim 1 and b) transform, in one or more steps, a compound of formula (Ill) to another of formula (I)

Throughout the description and claims the word "comprise" and its variants are not intended to exclude other technical features, additives, components or steps. To experts of the subject, other objects, advantages and features of the invention will become apparent in part from the description and practice of the invention. The following examples and figures are provided by way of illustration, and are not intended to be limiting of the present invention.

EXAMPLES

The invention will be illustrated by tests performed by the inventors, which shows the effectiveness of the compounds of the invention.

Example 1

Synthesis of the Compounds of the Invention

Synthesis Scheme for AX-105 to AX-108

Synthesis of compound AX-137: Mixture of Compound 1 (3 g, 1 eq), AgNO$_3$ (3.5 g, 2 eq.) in ethanol (30 ml) and NaOH (1.7 g, 4 eq.) dissolved in water (30 ml) was refluxed at 85° C. and stirred at this temperature for 4 h. The reaction was monitored by TLC. After completion the mixture was acidified with 1M HCl and extracted with DCM (2×30 ml). The combined organic layer was washed with water (20 ml), saline solution (10 ml) and dried over anhydrous sodium sulfate. Evaporation of the organic layer under reduced pressure yielded 1.5 g of the desired product with a purity of 96.2% by HPLC. $^1$H NMR (CDCl$_3$) δ 7.17-7.08 (m, 4H), 6.89-6.87 (d, 1H), 6.84-6.81 (m, 1H), 6.21-6.20 (d, 1H), 4.96 (s, 2H), 3.61 (s, 3H). Theoretic MS for C$_{17}$H$_{13}$FO$_4$: 300.28: M$^+$+1 found, 301.0.

Synthesis of compound AX-105: Mixture of AX-137 (0.2 g, 1 eq.), EDCl (0.14 g, 1.1 eq.), HOBt (0.09 g. 1 eq.), pyrrolidine (0.06 g, 1.2 eq.) and DIPEA (0.17 g. 2 eq.) in THF (5 ml) was irradiated by microwaves for 10 min. After this time the THF evaporated and the residue was washed with saturated sodium bicarbonate solution and extracted with DCM (2×10 ml). The combined organic layer was washed with water (20 ml), saline solution (10 ml) and dried over anhydrous sodium sulfate. Evaporation of the organic layer under reduced pressure yielded 135 mg of the desired product with a purity of 98% by HPLC. $^1$H NMR (CDCl$_3$) δ 7.37-7.33 (m, 2H), 7.10-7.06 (t, 2H), 6.89-6.87 (d, 1H), 6.78-6.75 (dd, 1H), 6.46-6.45 (d, 1H) 4.82 (s, 2H), 3.66 (s, 3H), 3.31-3.27 (t, 2H), 3.02 (b, 2H), 1.68-1.63 (m, 2H), 1.60-1.54 (m, 2H). Theoretic MS for C$_{21}$H$_{20}$FNO$_3$: 353.4; M$^+$+1 found, 354.1.

Synthesis of compound AX-106: Mixture of AX-137 (0.2 g 1 eq.). EDCl (0.14 g. 1.1 eq.), HOBt (0.09 g. 1 eq.) Etilamine, HCl (0.06 g. 1.2 eq.) and DIPEA (0.17 g. 2 eq.) in THF (5 ml) was irradiated by microwaves for 10 min. After this time the THF evaporated and the residue was washed with saturated sodium bicarbonate solution and extracted with DCM (2×10 ml). The combined organic layer was washed with water (20 ml), saline solution (10 ml) and dried over anhydrous sodium sulfate. Purification of the crude product by column chromatography (9% methanol in DCM) yielded 100 mg of the desired product with a purity of 99.3% by HPLC. $^1$H NMR (CDCl3) δ 7.29-7.27 (m, 2H), 7.20-7.15 (m, 2H), 6.89-6.86 (d, 1H), 6.79-6.76 (dd, 1H), 6.24-6.23 (d, 1H), 3.63 (s, 3H), 3.11-3.04 (q, 2H), 0.78-0.74 (t, 3H). Theoretic MS for C$_{19}$H$_{18}$FNO$_3$: 327.35: M$^+$+1 found, 328.1.

Synthesis of compound AX-107: Mixture of AX-137 (0.1 g 1 eq.), EDCl (0.07 g, 1.1 eq), HOBt (0.05 g, 1 eq.), N-methyl piperazine (0.04 g. 1.2 eq.) and D1PEA (0.09 g. 2 eq.) in THF (5 mL) was irradiated by microwaves for 10 min. After this time the THF was evaporated and the residue was washed with saturated sodium bicarbonate solution and extracted with DCM (2×10 ml). The combined organic layer was washed with water (20 ml), saline solution (10 ml) and dried over anhydrous sodium sulfate. Evaporation of the organic layer under reduced pressure yielded 68 mg of the desired product with a purity of 94.9% by HPLC. $^1$H NMR (CDCl3) δ 7.31 (b, 2H), 7.12-7.08 (t, 2H), 6.89-6.87 (d, 1H), 30 6.79-6.76 (dd, 1H), 6.44 (m, 1H), 4.95-4.91 (d, 1H), 4.68-4.64 (d, 1H), 3.66 (s, 3H), 3.5-3.7 (m, 3H), 3.04 (b, 1H), 2.3-2.27 (b, 1H), 2.13 (b, 4H), 2.03 (b, 1H), 1.49 (b, 1H). Theoretic MS for C$_{22}$H$_{23}$FN$_2$O$_3$: 382.4; M$^-$1 found, 383.0.

Synthesis of compound AX-108: Mixture of AX-137 (0.2 g, 1 eq), EDCl (0.14 g, 1.1 35 equiv), HOBt (0.09 g, 1 eq), N,N-dimethyl ethylene diamine (0.06 g, 1.2 eq) and DIPEA (0.17 g, 132 eq) in THF (5 mL) was irradiated by microwaves for 10 min. After this time the THF was evaporated and the residue was washed with saturated sodium bicarbonate solution and extracted with DCM (2×10 ml). The combined organic layer was washed with water (20 ml), saline solution (10 ml) and dried over anhydrous sodium sulfate. Purification of the crude product by column chromatography (6% methanol in DCM) yielded 80 mg of the desired product with a purity of 97.7% by HPLC. $^1$H NMR (CDCl3) δ 7.28-7.25 (m, 2H), 7.17-7.13 (t, 2H), 6.88-6.86 (d, 1H), 6.78-6.75 (dd, 1H), 6.22-6.21 (d, 1H), 5.80 (b, 1H), 3.63 (s, 3H), 3.13-3.09 (q, 2H), 2.08-2.05 (t, 2H), 1.97 (s, 6H). Theoretic MS for C$_{21}$H$_{23}$ClFN$_2$O$_3$: 370.42: M$^+$+1 found 371.0.

Synthesis Scheme for AX-129 to AX-132

A solution of NaClO$_2$ (1.07 g, 0.003 mol) and NaH$_2$PO$_4$ (1.63 g, 0.01 mol) in water (2.5 ml) was added to a solution of compound 1 (1.2 g, 0.003 mol) and 2-methyl-2-butene (3.92 ml, 0.037 mol) in t-BuOH (25 ml) at RT and stirred at same temperature till SM was consumed. After approx. 30 min, t-BuOH was evaporated and the resultant solution was acidifed using 2N HCl (pH=3-4). The resultant solid was filtered and vacuum dried to afford acid 2 as pale yellow solid (1.1 g, 88% yield) which was taken further for preparation of amides AX-129 to AX-132 without further purification. 1H NMR (CDCl3, 400 MHz) δ 7.23 (d, J=6.8 Hz, 1H), 7.13-7.07 (m, 3H), 6.88-6.80 (m, 2H), 6.23 (s, 1H), 4.94 (s, 2H), 3.58 (d, J=6.8 Hz, 2H), 1.13 (m, 1H), 0.58 (d, J=7.6 Hz, 2H), 0.25 (d, J=4.4 Hz, 2H). ES-MS [M−1]+: 339.1.

Synthesis of Compound AX-129:

EDCl (164 mg, 1.85 mmol) and HOBT (85 mg, 0.63 mmol) were added to a solution of acid 2 (194 mg, 0.57 mmol), pyrrolidine (32 mg, 0.45 mmol) and DIPEA (220 mg, 1.71 mmol) in THF (10 ml) and whole mixture was irradiated under microwave (900 W) for 4 min. THF was concentrated to minimum volume; the reaction mass was diluted with ice-cold water (20 ml) and extracted with EtOAc (3×25 ml). Combined organic extract was dried over Na2SO4 and concentrated on rotavapor to afford a crude residue which was purified by FCC ($SiO_2$, Hex-EtOAc mixtures) to produce the amide AX-129 (100 mg, 45% yield) as off-white solid. 1H NMR (DMSO-d6) δ 7.30-7.28 (m, 4H), 6.88-6.80 (m, 1H), 6.29 (s, 1H), 4.77 (s, 2H), 3.63 (d, J=6.8 Hz, 2H), 3.11 (m, 2H), 3.03 (s, 2H), 1.60-1.51 (m, 4H), 1.10 (m, 1H), 0.49 (d, J=8.0 Hz, 2H), 0.23 (d, J=4.4 Hz, 2H). ES-MS [M+1]+: 391.4.

Synthesis of Compound AX-130:

AX-130: AX-130 (130 mg, 76% yield) was prepared as pale yellow gummy solid starting from acid 2 (300 mg, 0.882 mmol) and replacing pyrrolidine in the above procedure with ethylamine. 1H NMR (DMSO-d6, 400 MHz): δ 7.63 (t, J=4.8 Hz, 1H), 7.27-7.25 (m, 4H), 6.87-6.79 (m, 2H), 6.17 (s, 2H), 4.78 (s, 1H), 3.61 (d, J=5.1 Hz, 2H), 2.9 (m, 2H), 1.08 (m, 1H), 0.69 (t, J=7.2 Hz, 3H), 0.48 (d, J=8.0 Hz, 2H), 0.22 (d, J=4.4 Hz, 2H). ES-MS [M+1]+: 368.1.

Synthesis of Compound AX-131:

AX-131: AX-131 (120 mg, 23% yield) was prepared as pale yellow gummy solid starting from acid 2 (200 mg, 0.588 mmol) and replacing pyrrolidine in the above procedure with N-methyl piperazine. 1H NMR (DMSO-d6, 400 MHz): δ 7.32 (m, 4H), 6.91-6.84 (m, 2H), 6.27 (s, 1H), 4.81 (s, 2H), 4.30 (m, 1H), 3.89 (m, 1H), 3.63 (d, J=6.8 Hz, 2H), 3.18 (m, 1H), 2.75-2.56 (m, 4H), 1.09 (m, 1H), 0.49 (d, J=8.0 Hz, 2H), 0.23 (d, J=4.4 Hz, 2H). ES-MS [M+1]+: 423.1.

Synthesis of Compound AX-132:

TBTU (514 mg, 1.6 mmol) was added to a solution of acid 2 (218 mg, 0.64 mmol) in mixture of CH2Cl2 (12 ml), DMF (2.5 ml) and DIEA (289 mg, 2.244 mmol) under N2; stirred at room temperature. After 1 h, 4-amino-1-methylpiperidine (221 mg, 1.923 mmol) was added and whole reaction mixture was stirred at room temperature for 6 h. The reaction mass was diluted CH2Cl2 (70 ml) and washed with water (2×25 ml). Organic layer was dried over Na2SO4 and concentrated on rotavapor to afford a crude residue which was purified by FCC (SiO2: MeOH—CH2Cl2 mixtures) to afford amide AX-132 (100 mg, 39% yield) as pale yellow oil. 1H NMR (DMSO-d6, 400 MHz): δ 7.58 (m, 1H), 7.28-7.26 (m, 4H), 6.16 (s, 1H), 4.78 (s, 2H), 3.61 (d, J=6.4 Hz, 2H), 3.45 (m, 1H), 2.62 (m, 4H), 2.21-2.00 (m, 6H), 1.43 (m, 2H), 1.40-1.00 (m, 6H), 1.08 (m, 1H), 0.48 (d, J=7.6 Hz, 2H), 0.21 (m 2H). ES-MS [M+1]+: 437.3.

Synthesis of the Compound AX-137:

AX-137: NaOH (1.7 g, 0.04 mol) dissolved in water (30 ml) was added to a stirred solution of aldehyde 3 (3.0 g, 0.01 mol), AgNO3 (3.5 g, 0.02 mol) in ethanol (30 ml) and the reaction mass was refluxed at 85° C. for 4 h. Reaction medium was acidified using 1M HCl (pH=2-3) and extracted with $CH_2Cl_2$ (2×70 ml). Combined organic extract was washed with saline solution solution (50 ml) followed by water (100 ml); dried over anhydrous Na2SO4 and concentrated to afford AX-137 (1.5 g, 47% yield). 1H NMR (CDCl3, 400 MHz) δ 7.17-7.08 (m, 4H), 6.89-6.87 (d, J=8.8 Hz, 1H), 6.83 (dd, J=8.8, 3.2 Hz, 1H), 6.21 (d, J=3.2 Hz, 1H), 4.96 (s, 2H), 3.61 (s, 3H). ES-MS [M+1]+: 301.0.

Example 2

Inhibition of T Cell Proliferation Induced by TCR Stimulation

Figure 1:
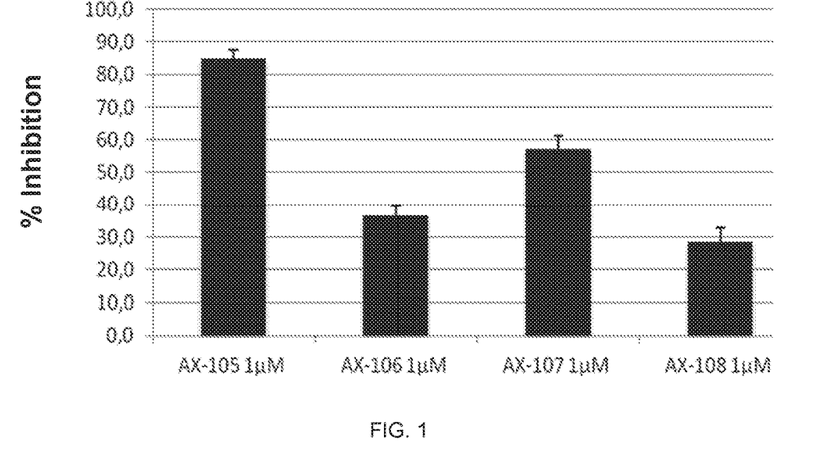
FIG. 1. Represents the ability of inhibiting the proliferation of T lymphocytes for each of the tested compounds AX-105, AX-106, AX-107 and AX-108 of the invention.

The effect of the compounds AX-105, AX-106, AX-107 and AX-108 on the ability of the TCR to induce proliferation of T lymphocytes was assessed in primary T lymphocytes obtained from the blood of healthy human donors (PBMC, peripheral blood mononuclear cells). The volunteers' PBMC were isolated by centrifugation of venous blood in Ficoll-Paque Plus density gradient. Purified cells (NWT; Nylon Wood T cells) were cultured in triplicate in 96-well plates ($0.5 \times 10^5$/well) in 200 ul of complete medium and stimulated with OKT3 (10 ug/ml) or with OKT3 (1 ug/ml) plus CD28 in the presence or absence of different compounds at the concentrations of 1 and 10 uM. The cultures were incubated for three days and analyzed after addition of 0.5 uCi [3H]TdR/well for the last 12 h of the culture. The radioactivity incorporated into DNA was determined by liquid scintillation counting. As cells divide, radioactivity is incorporated into daughter cells what allows having an idea of the degree of cell proliferation. The inhibition ability of the tested compounds is shown in FIG. 1.

Figure 2:
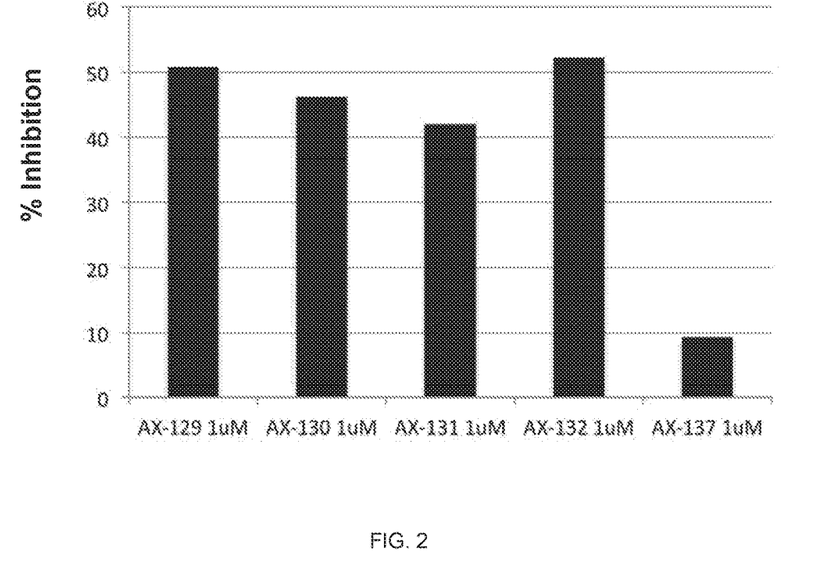
FIG. 2. Represents the ability of inhibiting the proliferation of T lymphocytes for each of the tested compounds AX-129, AX-130, AX-131, AX-132 and AX-137 of the invention.

Additionally, the effect of compounds AX-129, AX-130, AX-131, AX-132 and AX-137 was also analyzed in peripheral blood mononuclear cells (PBMCs) from healthy volunteers isolated by centrifugation of venous blood in Ficoll-Paque Plus density gradient. To purify T cells PBMC were passed through a nylon wood column. For cellular division analysis purified T cells were stained with carboxy-fluorescein succinimidyl ester (CSFE). Labeled cells ($0.5\times10^5$/well) were cultured in triplicate in 96-well plates in 200 ul of complete medium and stimulated with immobilized OKT3 (1 ug/ml) in the presence or absence of the test compounds mentioned before for 6 days and the percentage of proliferating cells (defined as CFSE low fluorescence) was determined by flow cytometry. The inhibitory ability of the tested compounds is represented in FIG. 2.

These assays allow the evaluation and confirmation of compounds abilities to inhibit T cell proliferation and therefore, contribute to the validation of such compounds as candidates for the development of new therapies for the treatment of autoimmune diseases mediated by T cells.

Example 3

In Vivo Test on Model of Type 1 Diabetes

The development of diabetes was monitored on a daily basis and recorded positive if levels of glucosuria are detected above 250 mg/dl in two consecutive measurements taken daily in the RIP-MOVA model or biweekly in NOD model. The effect of the treatment on disease incidence and survival was evaluated in the RIP-MOVA model as was for insulitis. Histopathologic evaluation of insulitis of sections H&E soaked in paraffin and fixed in formalin was assessed via a blind test by using the following classification system: stage 0, no invasion; stage 1, periinsulitis; stage 2, invasion >25%; stage 3, invasion >75%; and stage 4, the remaining islets. In a second phase, the therapeutic effect of the compounds was evaluated by treatment on RIP-mOVA mice once they have already developed diabetes. During this second phase, the compounds were tested in the NOD mice model.

The invention claimed is:

1. A compound having the structure of formula (I)

(I)

or a pharmaceutically acceptable salt, isomer or solvate thereof wherein:

$R_1$ is —$CH_3$ or —$CH_2$-cyclopropyl;

X —OH, —NHEt, or —$NHCH_2CH_2NMe_2$; and $R_4$ is F.

2. The compound according to claim 1, or a pharmaceutically acceptable salt, isomer or solvate thereof, wherein $R_1$ is —$CH_3$.

3. The compound according to claim 1, or a pharmaceutically acceptable salt, isomer or solvate thereof, wherein $R_1$ is —$CH_2$-cyclopropyl.

4. The compound according to claim 2, or a pharmaceutically acceptable salt, isomer or solvate thereof, wherein X is —NHEt.

5. The compound according to claim 3, or a pharmaceutically acceptable salt, isomer or solvate thereof, wherein X is —NHEt.

6. The compound according to claim 2, or a pharmaceutically acceptable salt, isomer or solvate thereof, wherein X is

7. The compound according to claim 3, or a pharmaceutically acceptable salt, isomer or solvate thereof, wherein X is

8. The compound according to claim 2, or a pharmaceutically acceptable salt, isomer or solvate thereof, wherein X is

9. The compound according to claim 3, or a pharmaceutically acceptable salt, isomer or solvate thereof, wherein X is 10. The compound according to claim 2, or a pharmaceutically acceptable salt, isomer or solvate thereof, wherein X is 11. The compound according to claim 3, or a pharmaceutically acceptable salt, isomer or solvate thereof, wherein X is 12. The compound according to claim 2, or a pharmaceutically acceptable salt, isomer or solvate thereof, wherein X is —NHCH$_2$CH$_2$NMe$_2$.

13. The compound according to claim 3, or a pharmaceutically acceptable salt, isomer or solvate thereof, wherein X is —NHCH$_2$CH$_2$NMe$_2$.

14. A compound selected from the group consisting of:
   (4-(4-fluorophenyl)-6-methoxy-2H-chromene-3-yl)(pyrrolidin-1-yl)methanone,
   N-ethyl-4-(4-fluorophenyl)-6-methoxy-2H-chromene-3-carboxamide,
   (4-(4-fluorophenyl)-6-methox-2H-chromene-3-yl)(4-methylpiperazin-1-yl)methanone,
   N-(2-(dimethylamino)ethyl)-4-(4-fluorophenyl)-6-methoxy-2H-chromene-3-carboxamide,
   (6-(cyclopropylmethoxy)-4-(4-fluorophenyl)-2H-chromene-3-yl)(pyrrolidin-1-yl) methanone,
   6-(cyclopropylmethoxy)-N-ethyl-4-(4-fluorophenyl)-2H-chromene-3-carboxamide,
   (6-(cyclopropylmethoxy)-4-(4-fluorophenyl)-2H-chromene-3-yl)(4-methylpiperazin-1-yl)methanone,
   6-(cyclopropylmethoxy)-4-(4-fluorophenyl)-2H-chromene-3-carboxylic acid,
   4-(4-fluorophenyl)-6-methoxy-2H-chromene-3-carboxylic acid, and
   6-(cyclopropylmethoxy)-N-(2-(dimethylamino)ethyl)-4-(4-fluorophenyl)-2H-chromene -3-carboxamide,
   or a pharmaceutically acceptable salt, isomer or solvate thereof.

15. The compound according to claim 2, or a pharmaceutically acceptable salt, isomer or solvate thereof, wherein X is —OH.

16. A pharmaceutical composition comprising a compound of formula (I) according to claim 1, or a pharmaceutically acceptable salt, isomer or solvate thereof, and one or more pharmaceutically acceptable excipients.

17. The compound according to claim 3, or a pharmaceutically acceptable salt, isomer or solvate thereof, wherein X is —OH.

18. A pharmaceutical composition comprising a compound according to claim 14, or a pharmaceutically acceptable salt, isomer or solvate thereof, and one or more pharmaceutically acceptable excipients.

19. A pharmaceutical composition comprising a compound according to claim 2, or a pharmaceutically acceptable salt, isomer or solvate thereof, and one or more pharmaceutically acceptable excipients.

20. A pharmaceutical composition comprising a compound according to claim 3, or a pharmaceutically acceptable salt, isomer or solvate thereof, and one or more pharmaceutically acceptable excipients.

* * * * *